United States Patent [19]

Steudle et al.

[11] Patent Number: 5,005,403
[45] Date of Patent: Apr. 9, 1991

[54] PROCESS AND APPARATUS FOR THE DETERMINATION OF THE CONCENTRATION OF A SUBSTANCE DISSOLVED IN A SOLVENT BY MEANS OF AN OSMOMETER

[75] Inventors: Ernst Steudle, Dorotheenstrasse 3, D-8581 Eckersdorf; Burkhard Stumpf, Trebgast, both of Fed. Rep. of Germany

[73] Assignee: Ernst Steudle, Eckersdorf, Fed. Rep. of Germany

[21] Appl. No.: 385,324

[22] Filed: Jul. 25, 1989

[30] Foreign Application Priority Data

Jul. 25, 1988 [DE] Fed. Rep. of Germany ....... 3825208

[51] Int. Cl.$^5$ ............................................ G01N 13/04
[52] U.S. Cl. ...................................................... 73/64.3
[58] Field of Search ......................................... 73/64.3

[56] References Cited

U.S. PATENT DOCUMENTS

| | | | |
|---|---|---|---|
| 3,063,288 | 11/1962 | Reiff | 73/53 |
| 3,187,562 | 6/1985 | Rolfson | 73/53 |
| 3,318,138 | 5/1967 | Rolfson | 73/64.3 |
| 3,518,875 | 7/1970 | Charmasson | 73/64.3 |
| 3,635,075 | 1/1972 | Gilbert | 73/64.3 |
| 3,661,011 | 5/1972 | Myrenne | 73/64.3 |
| 4,028,931 | 6/1977 | Bisera et al. | 73/64.3 |
| 4,245,495 | 1/1981 | Kakiychi et al. | 73/643 |
| 4,455,864 | 6/1984 | Wallner | 73/64.3 |
| 4,475,556 | 10/1984 | Reiff | 128/673 |
| 4,481,808 | 11/1984 | Sakata et al. | 73/61.1 |
| 4,706,495 | 11/1987 | Steudle et al. | 73/64.3 |

FOREIGN PATENT DOCUMENTS

| | | |
|---|---|---|
| 1845192 | 8/1961 | Fed. Rep. of Germany . |
| 2163640 | 6/1973 | Fed. Rep. of Germany . |
| 3525668 | 5/1986 | Fed. Rep. of Germany . |
| 3706361 | 9/1988 | Fed. Rep. of Germany . |
| 3736230 | 3/1989 | Fed. Rep. of Germany ....... 73/64.3 |
| 3825208 | 11/1989 | Fed. Rep. of Germany . |

OTHER PUBLICATIONS

"Membrane Osmometers", Mechrolab Inc., No CB1-4.
"GIT-Fachzeitschrift Für dal labroatorium", K. Derge (1966), 12:1097-1105.

Primary Examiner—Hezron E. Williams
Attorney, Agent, or Firm—Nils H. Ljungman & Associates

[57] ABSTRACT

In a process for the determination of the concentration of a substance dissolved in a solvent by means of an osmometer, comprising a two-chamber system with a first chamber having an osmosis cell and a second chamber for the measurement solution, to shorten the measurement time and to improve the separation of permeating components during the measurement of the concentration of the substances in the measurement solution, the pressure in the osmosis cell is held constant with an incompressible membrane arrangement, whereby with a pressure measurement apparatus in the second chamber after the replacement of a solvent, a reference solution or a calibration solution by a measurement solution, a pressure curve which corresponds to the concentrations of the nonpermeating substance and permeating substances or to the flows of the permeating substances between the osmosis cell and the second chamber is measured, and by analysis of the curve, the concentration of the nonpermeating and permeating substances in the measurement solution is determined. In one embodiment, the volume of the chamber containing the osmotic cell is varied in response to the pressure vs. time curve so as to maintain the volume flow of solvent through the membrane at substantially zero.

40 Claims, 9 Drawing Sheets

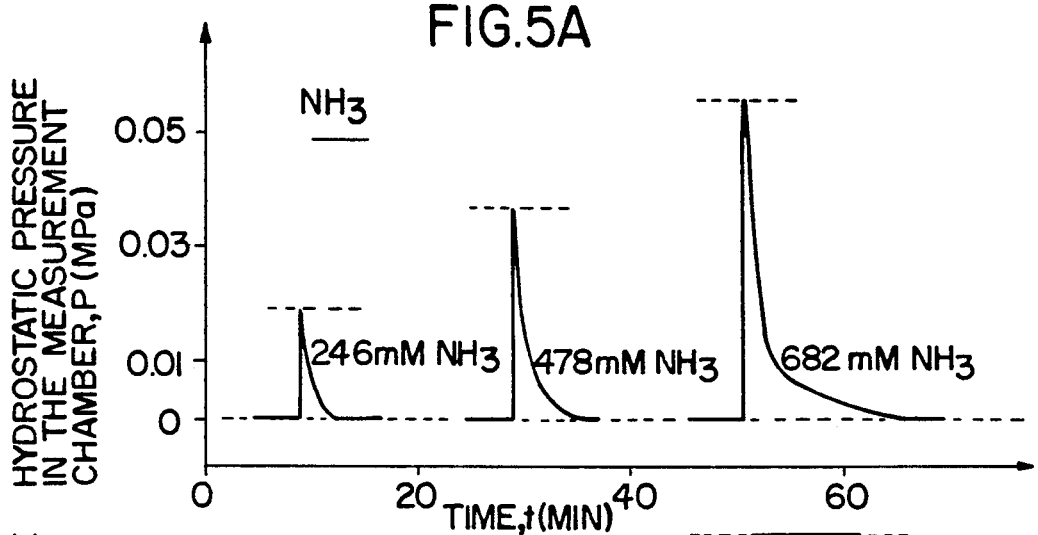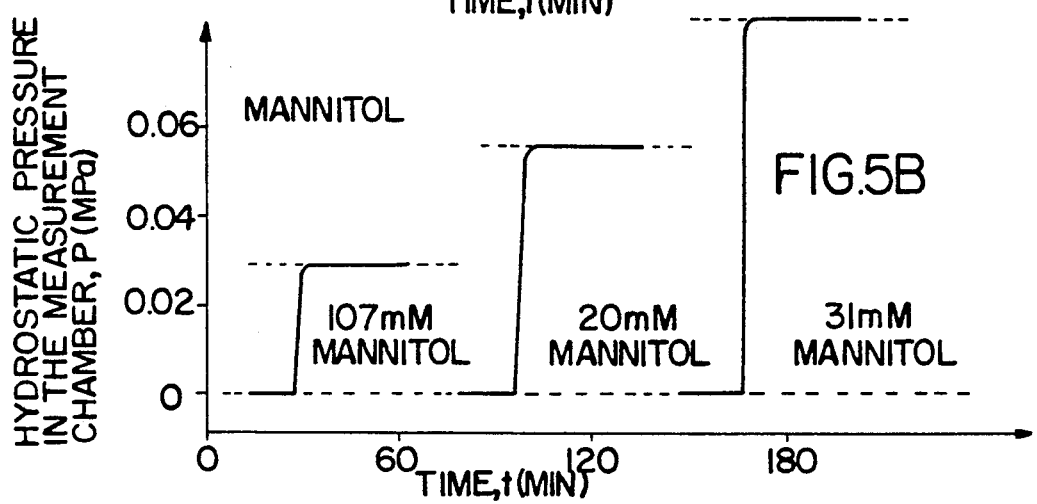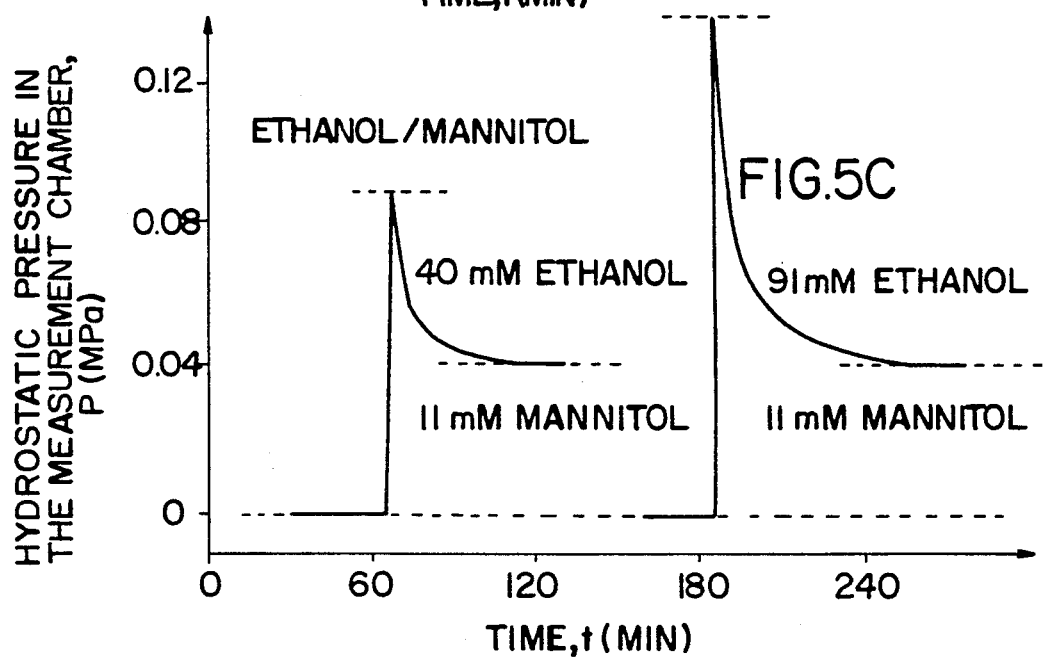

PROCESS AND APPARATUS FOR THE DETERMINATION OF THE CONCENTRATION OF A SUBSTANCE DISSOLVED IN A SOLVENT BY MEANS OF AN OSMOMETER

BACKGROUND OF THE INVENTION

1. Field of the Invention

The present invention relates to a process for the determination of the concentration of a substance (i.e., a solute) dissolved in a solvent by means of an osmometer, and to an apparatus for the execution of the process.

2. Description of the Art

Processes for determining the concentrations of solutes and apparatus for the implementation of the processes are described in U.S. Pat. No. 4,706,495 (which corresponds to German Laid Open Patent Application No. 35 25 668) and in German Patent Application No. P 37 06 361. In the processes described therein, an artificial osmosis cell is used as a sensor and contains a solution of a nonpermeating osmotic substance as a sensor. In the presence of a pure solvent (e.g., water), a constant hydrostatic pressure builds up in the cell, which is measured with an electronic pressure measurement sensor. In the presence of a measurement solution in a container, as a result of an osmotic volume flow out of the cell into the container, a pressure is obtained which changes with time, and which, in general, exhibits a two-phase curve, namely, one phase due to an osmotic water flow and another phase due to the flow of solutes. The concentration of dissolved substances is then determined from the curve.

This technique can be used principally for the determination of the concentrations of low-molecular substances in mixtures, whereby the selection of the membrane and coupling with chemical reactions makes possible a high degree of flexibility in its adaptation to defined measurement problems. For example, the concentration of solvents in waste water from the chemical industry can be measured using this process, as can the concentration of pollutants in solutions. Similarly, the decomposition products in bioreactors used in biotechnology processes can be directly determined. Other areas of application are the determination of alcohol concentration during alcoholic fermentation and the measurement of blood alcohol levels.

Such osmometers are also used to detect or to measure transport processes in plants and in the soil. They can also be used to simulate moisture stress situations, such as those which occur during drought or frost. The present invention is also intended for that field of application. With regard to related processes and the osmometers appropriate to them, reference is made to the above-referenced art.

For the determination of the concentration of a substance, both solutions with nonpermeating substances and those with permeating substances can be used. In the osmometer solution, a nonpermeating substance is used so that as a result of the osmotic pressure difference across the membrane in the osmosis cell, a hydrostatic working pressure builds up, which can be adjusted by using corresponding concentrations, such that, in the subsequent determination of the substance in the measurement solution, these differential pressures can be easily measured. For the adjustment, a reference solution is introduced into the measurement chamber which appropriately contains a pure solvent, e.g., water. After the determination of the working pressure $P_0$ in the osmosis cell, the reference solution placed in communication across the membrane is replaced sufficiently rapidly by the solution containing the substances to be determined, whereby the minimal pressure $P_{min}$ is established. Since this minimal pressure is determined by the concentration of the permeating substance in the solution, the exchange of the two solutions must occur very rapidly in relation to the half-time for the flow of the pure solvent through the membrane, which can be on the order of a few seconds.

The above-mentioned U.S. Pat. No. 4,706,495 also discloses alternative processes. The concentrations of the permeating and nonpermeating substances in the solution can also be determined on the basis of the pressure curve.

To be able to measure the concentration of certain substances in very small quantities, German Patent Application No. P 37 06 361 discloses a differential pressure process and apparatus, according to which a reference solution is selected which contains the same substances as in the solution to be measured, and in which the difference in the concentration between the reference and the osmometer solution is not greater than 70 mOsm. The process can also be refined by coupling it with a chemical reaction in the cell, e.g. an enzyme reaction, whereby a particularly high selectivity of the measurement system is achieved.

U.S. Pat. No. 3,635,075 discloses a so-called "Hepp" osmometer, in which the deformation of a pressure transformer membrane or a meniscus occurring as the result of a water flow is measured. To compensate for interferences by hydrostatic pressure differences on both sides of the membrane, there is a bypass, so that only the osmotic pressure is measured. The measurement principle employed is based on a change of the pressure or volume of an osmosis cell, i.e., water flows and volume changes take place in the osmosis cell.

In U.S. Pat. No. 4,706,495 (which corresponds to German Laid Open Patent Application No. 35 25 668), it is suggested that, with regard to a general control of the measurement head, not only for rigidity of the osmotic cells, but also in order to allow determination of the modulus of elasticity of the osmotic cell, it may be appropriate to provide an apparatus for effecting a controlled volume change of the osmotic cell. With such an apparatus, for example, the volume of the osmotic cell may be varied, within certain limits, by inserting and/or extracting a control rod. The resulting changes can be measured via a micrometer. With a closed osmotic cell, the resulting pressure changes may be detected by means of a pressure sensor, and therefore, with a known volume, the elasticity of the osmotic cell may be determined.

It has been determined that the processes and devices described above have disadvantages in terms of the measurement time and the separation of permeating components. In particular, substances whose permeability differs only slightly from that of the solvent are difficult to measure. Moreover, these processes have the disadvantage that the measurement times for the determination of the concentration are too long (25 minutes in the best case and several hours in the worst case for certain solutions).

REFERENCE TO OTHER APPLICATIONS

U.S. patent application Ser. No. 07/263,422, filed Oct. 27, 1988 and entitled "Process and Apparatus for the Selective Determination of the Concentration of a Substance Dissolved in a Solvent," which corresponds to German Patent Application No. 37 36 230.5, relates to subject matter similar to that of the present application, as does U.S. patent application Ser. No. 159,360, filed Feb. 23, 1988 and entitled "Process for the Determination of Concentration of Substances Dissolved in a Solvent by Means of Osmotic Cells," which corresponds to German Patent Application No. 37 06 361 discussed above.

The above-mentioned U.S. Pat. Nos. 3,635,075 and 4,706,495 and German Patent Applications Nos. 35 25 668, 37 06 361 and 37 36 230.5 are hereby expressly incorporated by reference, with the same effect as if they were fully set forth in their entirety herein.

OBJECTS OF THE INVENTION

One object of the present invention is the provision of an alternative measurement process which permits shorter measurement periods.

Another object of the present invention is the provision of a process and apparatus for the quick and accurate determination of the concentration of a solute dissolved in a solvent.

In one aspect of the invention, it is preferred that two pressure measurement devices be employed, one to determine the pressure existing in the measurement chamber and one for determining the pressure existing in the osmotic cell. However, in another aspect of the invention disclosed herein, only a single pressure measuring device associated with the osmotic cell is required. Naturally, in this embodiment, a second pressure measuring device associated with the measurement chamber can be additionally employed if desired, for example, in order to utilize a large area pressure sensor for increased sensitivity. Preferably, the pressure measuring devices employed include means for converting the measured pressure into electrical information signals for processing.

SUMMARY OF THE INVENTION

As a general rule, the measurement chamber has a volume larger than that of the osmosis cell. The present inventors have discovered therefore, that pressure sensors with a larger surface area and which are therefore more sensitive can be installed inside it. These pressure sensors are a component of a pressure transformer, e.g. an electronic pressure transformer which converts the pressure measured into electrical signals which can be evaluated.

In a process described herein, the measurement time can be significantly shortened. Likewise, the concentrations of substances in measurement solutions can be determined even if their permeability differs only slightly from that of the solvent.

According to one aspect of the invention, by means of a compensation process, the volume flows (Jv) which occur during the replacement of the reference solution in the measurement chamber by the measurement solution are prevented or eliminated, in that the pressure in the test chamber is increased or decreased so that a constant pressure in the osmosis cell is maintained. In this manner, the measurement principle and the character of the measurement curves are modified, so that the pressure curve in the measurement chamber no longer reflects volume flows, but substantially directly reflects the solute or particle flows.

The differential values determined by the measurement apparatus in the measurement chamber are sensed during the measurement time and can be represented in the form of curves. An evaluation of the measurement curves is thereby significantly simplified by the compensation process, since, in relation to the working pressure established, there is a sudden increase which is substantially maintained in the measurement of the concentration of the substance in a solution which contains only nonpermeating substances. If, on the other hand, after the determination of the maximum pressure, the pressure decreases exponentially, this provides an indication that permeating substances are present, the concentrations of which can be determined by means of the curve.

If more than a permeating substance is present in the measurement solution, and if there is an appropriate membrane which is permeable for the substances, then, from the differential curves or from the initial slopes, by means of the exponential functions corresponding to the individual segments, it is possible to determine not only the concentration of the permeating substances, but also their composition, and their nature, by means of reference values. This can be appropriately accomplished by means of a computer program. The concentrations of permeating and nonpermeating substances can be determined directly from the maximum changes registered by the pressure measurement apparatus.

In preferred embodiments, the quantitative evaluation is performed after calibration with solutions having known concentrations or by calculation, as indicated above. Devices which have been found to be particularly well-suited for the performance of the process and advantageous refinements of these devices are described herein.

The pressure compensation can be achieved in a number of different ways. A device which enables such pressure compensation and which is appropriate for the execution of the process is described herein. For example, the pressure can be set directly by varying or increasing the pump pressure and then closing the feed valves with the discharge valve closed. However, it can also be adjusted by changing the volume of the measurement chamber. As a regulating variable, the pressure in the osmosis cell is measured, and is increased corresponding to the pressure decrease caused by the volume flow of the solvent or of the permeating substances of the defined osmotic solution, whereby a volume flow of the solvent in the osmotic solution and thus a pressure decrease in the osmosis cell is prevented. As a rule, this process takes only a few minutes, such that, even with a measurement time of 10 to 15 minutes, the pressure curve established by the volume flow of the substances in the measurement chamber makes possible a determination of the concentration of the permeating and nonpermeating substances. Morever, concentrations can be determined from the maximum values of the pressure in the measurement chamber, following a calibration. Then, the measurement times are only approximately on the order of 10–20 seconds. The working temperature is 21.5° C.

The process gives a qualified evaluation of the pressure values determined, if a pressure change in the two chambers is not adversely affected by the mechanical configuration of the membrane. Preferably, the membrane should be designed rigidly enough so that it does not deform or bow under the specified pressure differences between the two chambers. It is therefore recommended that the membrane be supported by a support grid, or that a nondeformable and incompressible porous body of sintered glass material ceramic or plastic be used, and that an underpressure or negative pressure be created in the osmosis cell, such that even a nonrigid membrane is held in contact under pressure with the surface of the osmosis cell. The osmosis cell can also be already saturated with a solution, or can include a solution film.

Basically, the process can be used for the determination of the concentration of permeating and nonpermeating substances in solutions of greatly varied composition. Moreover, the differential process described in German Patent Application No. P 37 06 631 can also be used to refine the process.

The evaluation of the measured pressure curve in the measurement chamber can be appropriately performed by means of a computer. The digitized measurements or the analog electrical measurements from the pressure transformer are fed to the measurement pickup inputs of the computer and are converted to digital values for processing. The measurement curves are evaluated on the basis of a program stored in the computer, and determinations of the concentration of individual substances can be made directly on the basis of the differential exponential curves and corresponding reference values, if a membrane is selected which is appropriately permeable for different substances.

In an alternative embodiment of the invention described herein, the osmotic cell is provided with a regulating rod or plunger which can be moved relative to the interior of the osmotic cell in a number of ways, for example, manually by hand, through a micrometer screw or by means of a motor or a hydraulic drive, in order that the hydrostatic pressure acting in the osmotic cell may be either increased or decreased. During the measurement phase of the process, the regulating rod or plunger is manipulated such that the volume (e.g., solvent) flow through the membrane is maintained at a substantially zero value. In such case, the change of stationary pressure which is observed becomes a measure of the concentration of solute (i.e., nonpermeating and/or permeating), as compared with a reference pressure determined by introducing a reference solution (e.g., solvent) into the measurement chamber.

The hydrostatic pressure of the osmotic cell is controlled via the regulating rod or plunger, so as to maintain the pressure flow (dP/dt) or respectively, the volume flow of the solvent (dv/dt) at a substantially zero value. For example, if there is an increase in the concentration of the solute in the solution to be measured with respect to the reference solution of a known concentration, the hydrostatic pressure acting in the osmotic cell may be lowered by means of the regulating rod or plunger so as to maintain the above-noted conditions of zero change with respect to time. Conversely, if the solute is present in a decreased concentration in the solution to be measured, the hydrostatic pressure acting on the osmotic cell can be increased via the same regulating rod or plunger. Accordingly, it will be appreciated that this aspect of the invention, which requires only one pressure measuring device associated with the osmotic cell, and wherein the pressure change (dP/dt) and respectively, the volume flow of the solvent (dv/dt) are maintained to be substantially zero, is a species of the more generic aspect of the invention disclosed herein, and can be used to measure the concentrations of both nonpermeating and permeating substances. When the procedure is used to measure the concentrations of permeating substances, the resulting pressure vs. time curves are two-phased, e.g., during an increase of the concentration, a particle phase will be exhibited after a minimum has been attained, the length of which, in contrast to other embodiments described herein, cannot be influenced.

Use of the procedure wherein the volume of the chamber containing the osmotic cell is varied allows a reduction of the required measurement time from about a few minutes to about 20 seconds. It is not required that a substantially incompressible osmotic cell be used. It is, however, recommended that the osmotic cell be equipped with a high degree of rigidity (e.g., have a high elastic coefficient) and have a substantially high surface area to volume ratio. Moreover, an additional advantage of this procedure is that changes of concentration within the cell are largely avoided by the compensation process.

Still further, this procedure finds important applicability in situations wherein the half-life for the exchange of the solute is significantly greater than for that of the solvent (e.g., water).

Preferably, the regulating rod or plunger has a diameter on the order of 0.5 mm and is positioned within a cylinder which adjoins the chamber in which the osmotic cell is located, such that the regulating rod or plunger can be reciprocately translated, in order that the relationship of the momentarily recorded pressure value can be further adjusted to a point where the volume flow through the membrane (e.g.,dP/dt) becomes substantially zero in value.

One aspect of the invention resides broadly in a process for testing a test solution, the test solution including a solvent and at least one solute dissolved in the solvent, the process employing a first chamber, a second chamber and a membrane interposed between the first and second chambers, the process including the steps of introducing an osmometer solution into the first chamber: introducing a reference solution into the second chamber; determining a reference pressure $P_O$ established in one of the first and second chambers: replacing the reference solution in the second chamber with the test solution; maintaining a constant fluid pressure in one of the first and second chambers; determining at least one pressure change characteristic occurring in the other of the first and second chambers; and using the at least one determined pressure change characteristic to determine the concentration of the at least one solute dissolved in the solvent.

Another aspect of the invention resides in a process for the determination of the concentration of a solution to be tested which includes at least one substance dissolved in a solvent. The process includes providing a first chamber and a second chamber; interfacing the first and second chambers through a membrane; introducing an osmometer solution into the first chamber; introducing the solution to be tested into the second chamber; compensating for fluid pressure changes in at least one of the first and second chambers; determining at least one pressure change characteristic occurring in at least one of the first and second chambers; and using the at least one determined pressure change characteristic to determine the concentration of the at least one substance dissolved in the solvent.

Still another aspect of the invention resides in an apparatus for the determination of the concentration of a solute dissolved in a solvent, the apparatus including a first chamber; a second chamber; a membrane interposed between the first and second chambers; apparatus for introducing, selectively, into the second chamber, a reference solution and the solute dissolved in the solvent; a pressure maintenance device for maintaining a constant pressure in one of the first and second chambers; and a pressure sensor device for sensing the fluid pressure in the other of the first and second chambers.

Still another aspect of the invention resides in a process for the determination of the concentration of a test solution, the test solution including at least one solute dissolved in a solvent, the process employing a first chamber, a second chamber, a membrane interposed between the first and second chambers, compensation device for compensating for the volume flow of at least the solvent through the membrane and between the first and second chambers, and a pressure sensing device for sensing at least one pressure existing in the first chamber, the process including the steps of introducing an osmometer solution into the first chamber: introducing a reference solution into the second chamber; determining a reference pressure $P_O$ established in one of the first and second chambers; replacing the reference solution in the second chamber with the test solution; employing the compensation device for compensating for the volume flow of at least the solvent through the membrane; employing the pressure sensing device for determining at least one pressure change characteristic occurring in the first chamber; and using the at least one determined pressure change characteristic occurring in the first chamber to determine the concentration of the at least one solute dissolved in the solvent.

A further aspect of the invention resides broadly in an apparatus for the determination of the concentration of a test solution, the test solution comprising a solute dissolved in a solvent, the apparatus including a first chamber: a second chamber; a membrane interposed between the first and second chambers; device for introducing an osmometer solution into the first chamber; device for introducing, selectively, into the second chamber, a reference solution and the test solution; a pressure sensing device for sensing the pressure existing in the first chamber and for generating signals representative thereof; and a compensation device for compensating for the volume flow of at least the solvent through the membrane and between the first and second chambers.

BRIEF DESCRIPTION OF THE DRAWINGS

The invention is explained in greater detail below, with reference to the embodiments and the curves illustrated in the accompanying drawings, wherein:

FIGS. 5A, 5B, and 5C are pressure vs. time plots resulting from working embodiments set forth herein;

DESCRIPTION OF THE PREFERRED EMBODIMENTS

An apparatus according to one aspect of the invention essentially consists of a closed housing 1 having rigid walls, with thick, pressurizeable walls, a chamber 2 inside housing 1 for holding an osmosis cell 17, 18 (shown in more detail in FIGS. 2 and 3), which completely fills up the chamber 2, and a chamber 3 which forms the measurement chamber.

Figure 2:
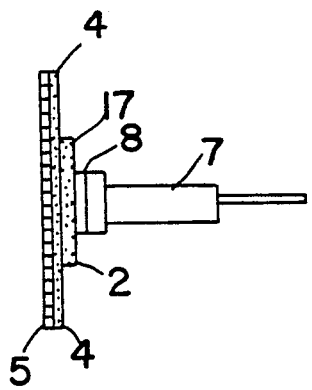
FIG. 2 is an elevational view of a membrane, an osmosis cell and a pressure transducer employed in one embodiment of the invention.
Figure 3:
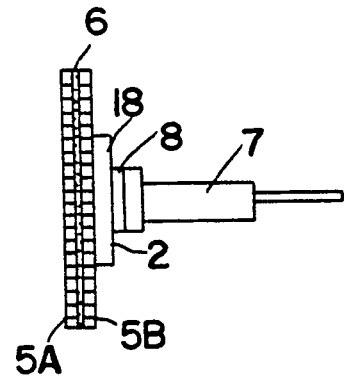
FIG. 3 is an elevational view of a membrane, an osmosis cell and a pressure transducer employed in another embodiment of the invention.

The two chambers 2 and 3 are separated from one another by a membrane 4, which, as shown in FIGS. 2 and 3, is supported by a support grid 5. In direct contact with this membrane is the osmosis cell 17 and 18 in FIGS. 2 and 3, respectively, which can consist, for example, of a thin ceramic chip (in the embodiment of FIG. 2), provided that care is taken that the support grid 5 prevents a deflection of the membrane in either direction. For this purpose, FIG. 3 shows a double support grid 5A and 5B with a membrane 6 positioned therebetween. Fastened to the osmosis cell 17 or 18 is a pressure transformer 7 which is positioned by a housing wall of the housing 1, having a sensor 8 which measures the hydrostatic pressure in the osmosis cell. In the pressure transformer 7, the pressure measured is electronically converted into electrical signals, preferably digitally encoded signals, which are transmitted to the measurement input of a central computer 9.

This central computer 9 simultaneously serves as the central control unit for the activation of a reducer valve 10 in the output line of the measurement chamber 3, and for the control of a pump 11 in the feed line. There are corresponding control outputs on the central computer 9. The pump 11 is located in the feed line 12. Immediately ahead of the inlet there is a cutoff valve (not shown). The latter can be electrically or pneumatically opened or closed as a function of corresponding control commands from the central computer 9.

The osmometer according to the invention can also be used in the flow-through process, if the pressure can be set by means of a reducer valve. For example, it can be installed in a bypass on a principal pipeline, through which the measurement fluid flows continuously. In such case, preferably, the valves are used only for the calibration or reference value process.

A pressure sensor 13 of an additional pressure transformer 14 engages the measurement chamber 3, in order to determine the instantaneous pressure in the measurement chamber 3, and transmits appropriately electronically digitized measurements to another measurement input of the central control unit 9.

In the test chamber, the pure solvent, the solution to be measured or the calibration solutions can be moved by a circulation pump. The hydrostatic pressure in the measurement chamber 3 is recorded by the pressure sensor 13 and converted by the pressure transformer into data which can be processed by the central control unit 9. The osmosis cell can thereby be charged with a nonpermeating substance, either via the second chamber 3 or via feed lines, whereby, in the presence of a pure solvent in the adjacent measurement chamber 3, a constant hydrostatic working pressure $P_0$ builds up at atmospheric pressure in the osmosis cell.

After a replacement of the reference solution by a solution to be measured or a calibration solution, a water (volume) flow out of the osmosis cell takes place, which leads to a pressure drop in the osmosis cell. The water flow is compensated by counter control, for example, by a pressure increase in the measurement chamber 3, for which purpose a not-yet-closed reducing valve is placed in a position which makes a pressure increase possible.

In another embodiment, the pressure is increased by changing the volume of the measurement chamber 3, for which purpose appropriate movable displacement elements are located in the walls, which can be moved by drive systems, for example, a piston which can be adjusted by means of a micrometer screw. Such movable displacement elements, together with associated drive systems are well known in the art of mechanical design. For example, hydraulically positionable pistons could be deployed such that they would, under control of the computer 9, project into the measurement chamber 3 to effect the desired pressure increase.

Figure 4A:
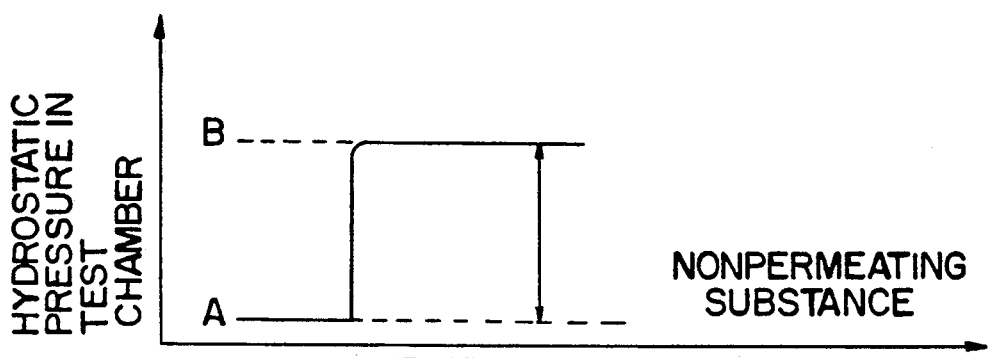
FIGS. 4A, 4B, and 4C are simplified pressure vs. time plots indicating the general pressure variations caused by different solutes.

If the measurement solution consists only of one nonpermeating substance, then one pressure stage is recorded, i.e. the maximum pressure established which is used to compensate the force of the volume flow, which is a direct indication of the concentration of the nonpermeating substance in the solution to be measured. A typical pressure curve for such a situation is shown in FIG. 4A. By means of the pressure transformer 14 with the sensor 13, ignoring the transition time, a pressure increase is produced in the pressure chamber to a new, constant level (from A to B), which is proportional to the concentration of the nonpermeating substance.

Figure 4B:
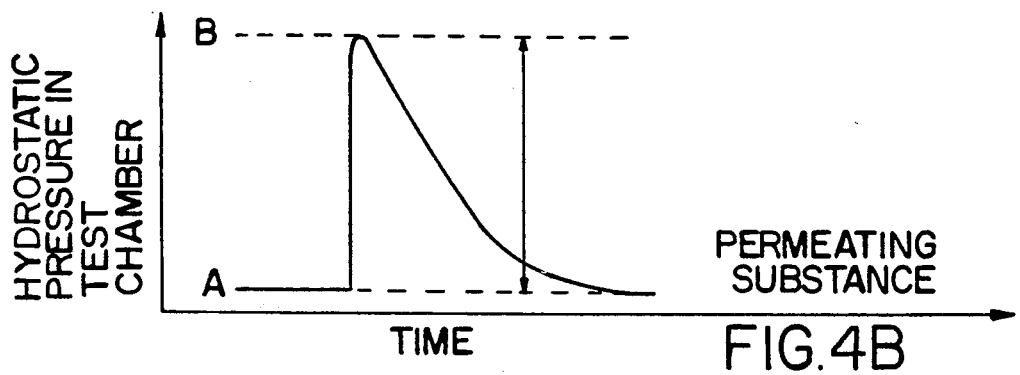

If the measurement solution includes only one or more permeating substances, then, after the compensation, there is also a proportional pressure increase, but one which is then followed by an exponential pressure decrease to the old level, as the substance(s) permeates into the osmosis cell, as shown in FIG. 4B. The rate constant of the pressure decrease is a material constant for a given membrane and a given solvent. From the differential curve segments having different slopes, the exponential curves of the individual permeable substances can be calculated, if they are simultaneously evaluated with a corresponding membrane arrangement. For a permeating substance, the initial slope can also be used as a yardstick for the concentration. From the differential values, the central computer 9 can then be used to determine the exponential functions which correspond to a specified substance, so that a substance analysis is possible with a simultaneous determination of the concentration, if reference values for that purpose are stored in the central processing unit or in another connected computer.

Figure 4C:
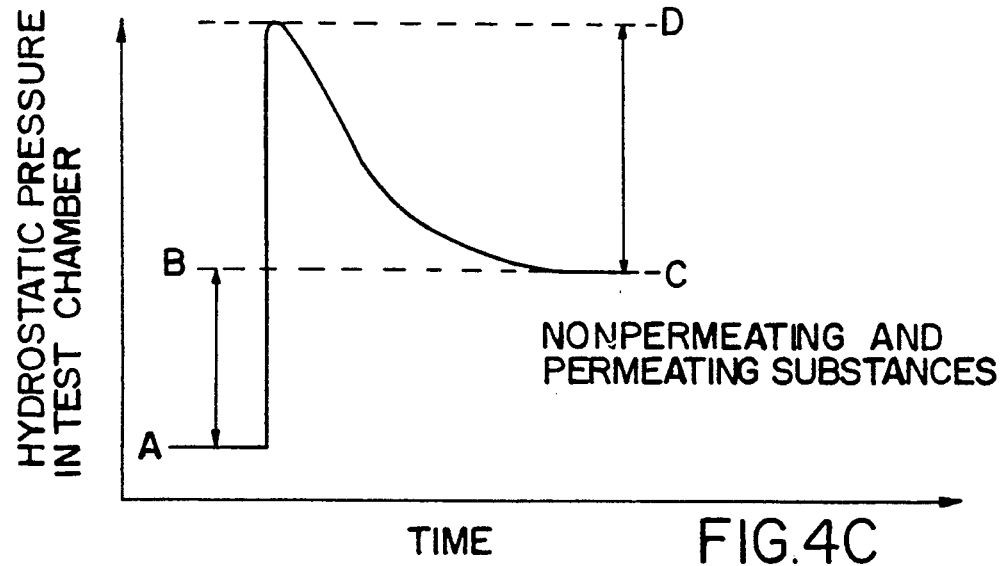

On the other hand, if a mixture of a permeating substance and a nonpermeating substance is present, there is a superimposition of the two processes described above, which are appropriately recorded by the pressure transformer, as shown by Curve C in FIG. 4, whereby the segments A/B and C/D, which indicate pressure changes, serve as a yardstick for determining the concentrations of the nonpermeating substance and of the permeating substance, which can be determined either by calculation or by calibration with solutions of known concentrations. Several permeating substances can be determined one after the other, if their rate constants differ sufficiently from one another.

Instead of a pure solvent (e.g., water), in the practical application described here, a reference solution can also be used with concentrations and indications according to the process described in German Patent Application No. P 37 06 361. This allows the process described herein to be used to measure extremely fine differences in concentration.

The osmometer solution can also be introduced directly into the osmosis cell. Different configurations of the two chambers in a closed system are possible, and can be adapted to fit the application at hand. The curve can preferably be displayed by means of an analog display apparatus 15, which can be connected to the central control unit 9. Likewise, if a computer-support evaluation is used, the corresponding concentrations of the substances in the solution to be measured can preferably be displayed on a printer 16.

When sizing the measurement chambers, there are no upper limits to the reasonable size of the measurement chamber, as long as it is guaranteed that there is no pressure gradient inside the measurement chamber, which would lead to a pressure applied to the pressure transformer which differs from the pressure applied to the membrane. To increase the measurement sensitivity, the osmosis cell should have a large effective surface, a small volume (a layer thickness of, for example, 0.2 mm) and a high hydraulic conductivity.

Figure 6A:
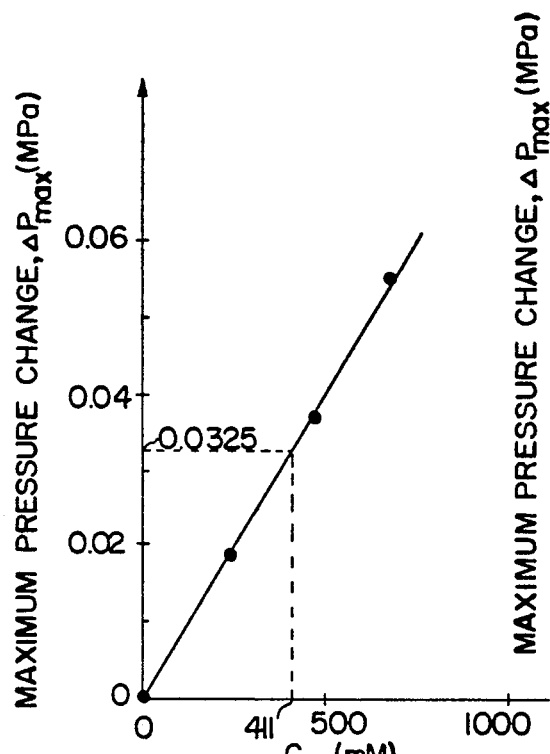
FIGS. 6A and 6B are pressure change vs. concentration plots derived from working embodiments set forth herein and illustrating a substantially linear relationship therebetween.

The following preferred process embodiments illustrate the areas in which the invention is preferably used, and the corresponding measurement processes:

Preferred Process Working Embodiments (A) Determination of the Concentration of a Permeating Substance in a Solvent from the Maximum Pressure Change (FIGS. 5A and 6A):

Permeating substance: Ammonia ($NH_3$): solvent: water. The addition of various concentrations of $NH_3$ to the reference solution (water) produces monophase relaxations, whereby the maximum pressure change ($\Delta P_{max}$) is proportional to the concentration, as shown in FIGS. 5A and 6A. During calibration, the following values were determined:

| $C_{NH_3}$(mM) | 246 | 478 | 682 |
|---|---|---|---|
| $\Delta P_{max}$(MPa) | 0.0184 | 0.0368 | 0.0554 |

The determination of the concentration of a particular aqueous NH₃ solution gave a $\Delta P_{max} = 0.0325$ MPa, which, on the basis of the calibration lines, indicates a corresponding concentration of $C_{NH_3} = 411$ mM, as shown in FIG. 6A.

(B) Determination of the Concentration of a Nonpermeating Substance in a Solvent (FIGS. 5B and 6B):

Nonpermeating substance: Mannitol; solvent: water. The addition of various concentrations of mannitol to the reference solution (water) produced pressure stages with a constant $\Delta P_{max}$ maintained in the measurement chamber, with $\Delta P_{max}$ being reached after approximately 40 seconds. [See FIG. 5B.] The following values were measured during calibration:

| $C_{Mannitol}$(mM) | 10.7 | 20 | 31 |
|---|---|---|---|
| $\Delta P_{max}$(MPa) | 0.0298 | 0.0556 | 0.0850 |

Figure 6B:
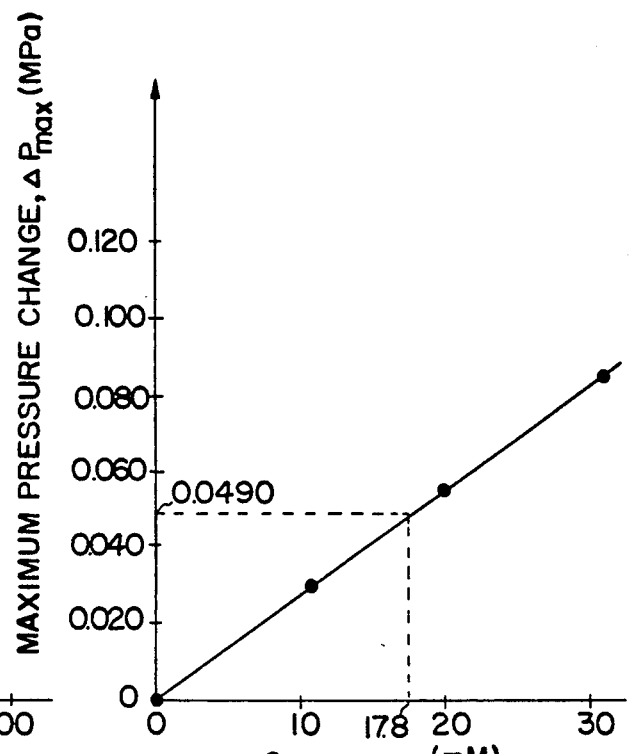

The determination of the concentration of a particular aqueous solution of mannitol gave a $\Delta P_{max} = 0.0490$ MPa, which corresponds a concentration $C_{imp} = 17.8$ mM, as shown in FIG. 6B.

(C) Determination of the Concentration of a Permeating and a Nonpermeating Substance Mixed with One Another (FIG. 5C):

Permeating substance: ethanol: nonpermeating substance: Mannitol. The addition of mixtures of ethanol and mannitol produced monophase pressure relaxations with constant pressure stages, as shown in FIG. 5C, whereby the levels of the pressure stages and $\Delta P_{max}$ were in turn proportional to the concentration.

Figure 7A:
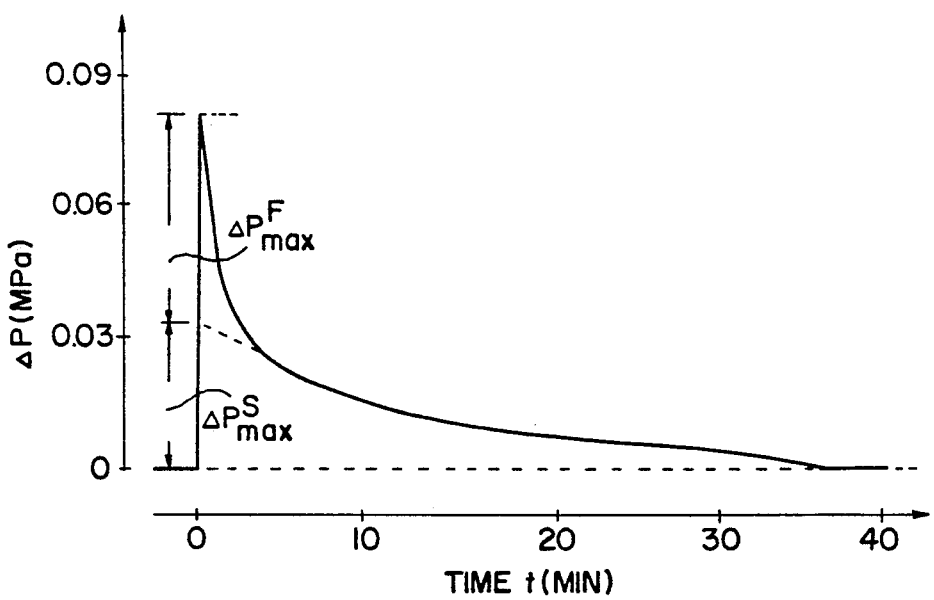
FIG. 7A is a pressure vs. time plot resulting from a working embodiment utilizing two permeating substances and described herein.

(D) Solution with Two Permeating Substances (FIGS. 7A, 7B and 7C):

Permeating substances: NH₃ and propanol-1; Solvent: water. The addition of a mixture of a relatively rapidly permeating substance (NH₃) and a relatively slowly permeating substance (propanol-1) produced biphase relaxations with a fast component (rate constant: $k_F$ [K-fast]) and a slow component (rate constant: $k_S$ [K-slow]). After a sufficient passage of time t after the addition, the pressure decrease is determined practically only by $k_S$, since the rapidly permeating substance is then at equilibrium. The distinctly differing rates of biphase relaxation are clearly shown in FIG. 7A.

Figure 7B:
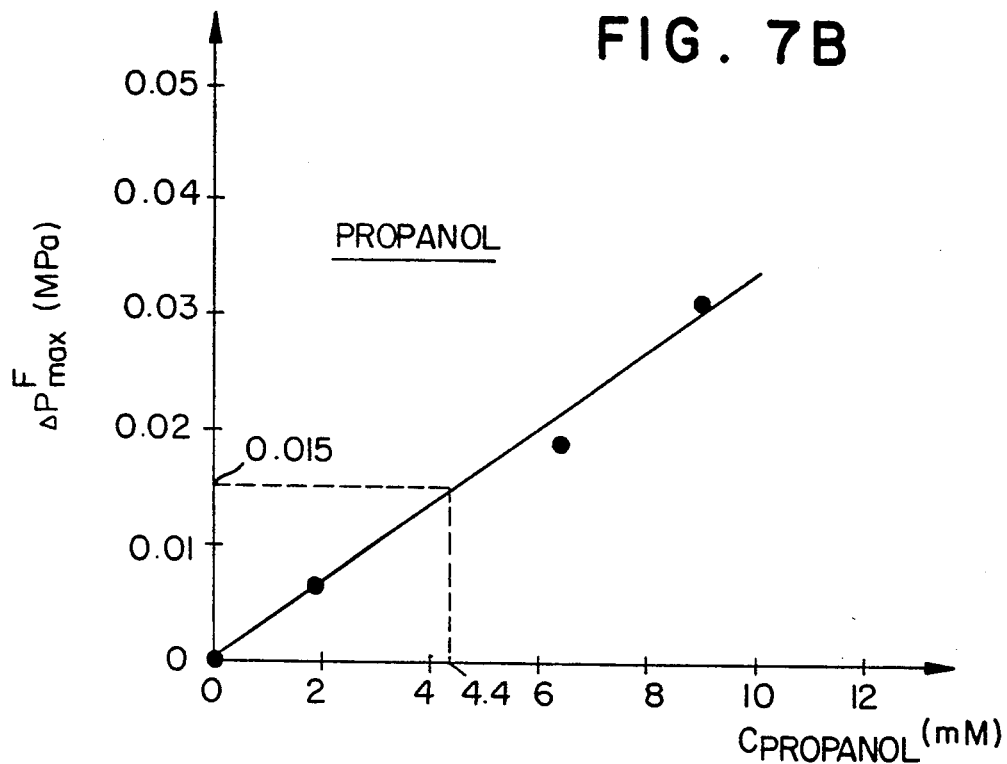
FIGS. 7B and 7C are similar to FIGS. 6A and 6B described above.

Using a semilogarithmic plotting over time, we also get for these times, from the slope $k_S$ and by extrapolation to $t=0$, the initial value, $\Delta P_{max}^S$, of propanol-1. After calibration, this then also yields $C_{Propanol}$, as shown in FIG. 7B. We have:

$$\Delta P^S = \Delta P_{max}^S \cdot \exp(-k_S t) \quad (1)$$

and $$C_{Propanol} = K_{Propanol} \cdot \Delta P_{max}^S \quad (2)$$

It is also possible to obtain a relationship for the rapidly permeating substance corresponding to Equation (1) by subtraction, since $$\Delta P^F = \Delta P_{max}^F \cdot \exp(-k_F t) \quad (3)$$

and $$C_{NH_3} = K_{NH_3} \cdot \Delta P_{max}^F \quad (4)$$

The calibration was performed with solutions of various concentrations of NH₃ and propanol-1, which yielded the following calibration points:

| $C_{NH_3}$(mM) | 276 | 553 | 826 |
|---|---|---|---|
| $\Delta P_{max}^F$(MPa) | 0.170 | 0.359 | 0.486554 | and

| $C_{Propanol}$(mM) | 2.0 | 6.5 | 9.0 |
|---|---|---|---|
| $\Delta P_{max}^S$(MPa) | 0.060 | 0.192 | 0.322 |

Figure 7C:
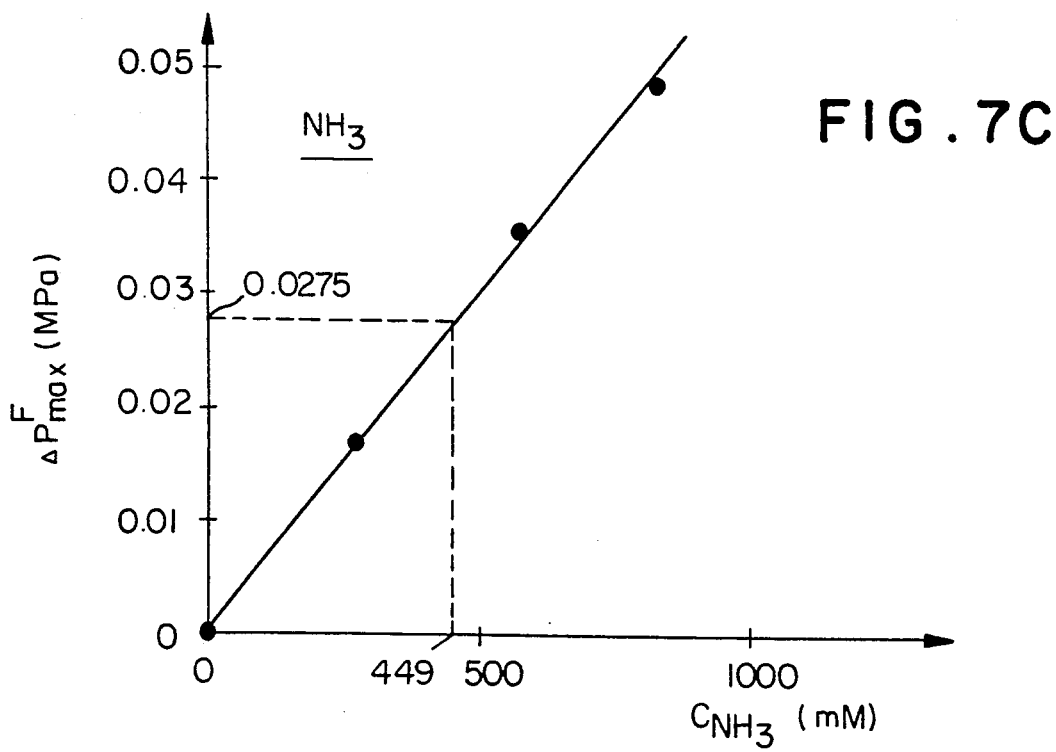

In a particular mixture, $\Delta P_{max}^S = 0.0015$ MPa and $\Delta P_{max}^F = 0.0275$ MPa were determined, which yielded the corresponding concentrations of $C_{Propanol} = 4.4$ mM and $C_{NH_3} = 449$ mM. [See FIGS. 7B and 7C.]

(E) Determination of the Concentrations of Permeating Substances from the Initial Slope [(dP/dt)t=0](FIGS. 8A, 8B and 8C):

The present inventive process can be used to determine the concentration of a permeating substance in the presence or in the absence of nonpermeating substances. (dP/dt) at $t=0$ for a given membrane and a constant temperature is proportional to the permeability of the substance, the effective surface/volume ratio of the osmosis cell and the concentration, so that:

$$(dP/dt)_{t=0} = K \cdot C \quad (5)$$

Figure 8A:
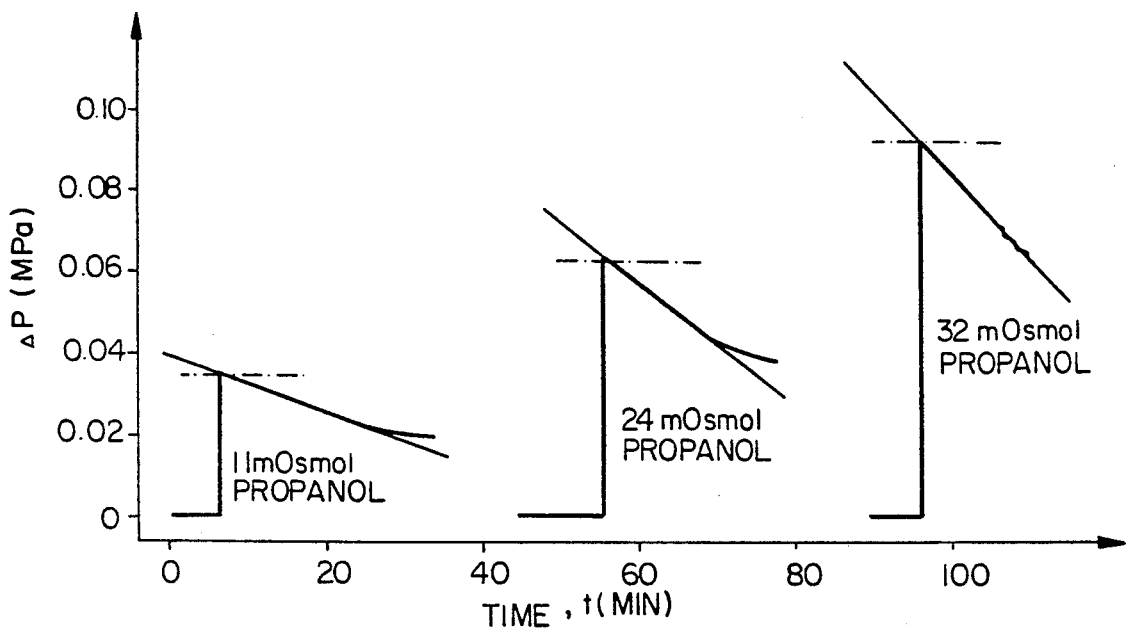
FIG. 8A is a pressure vs. time plot derived from a working embodiment disclosed herein and illustrating the derivation of $dP/dt$ at $t=0$.
Figure 8B:
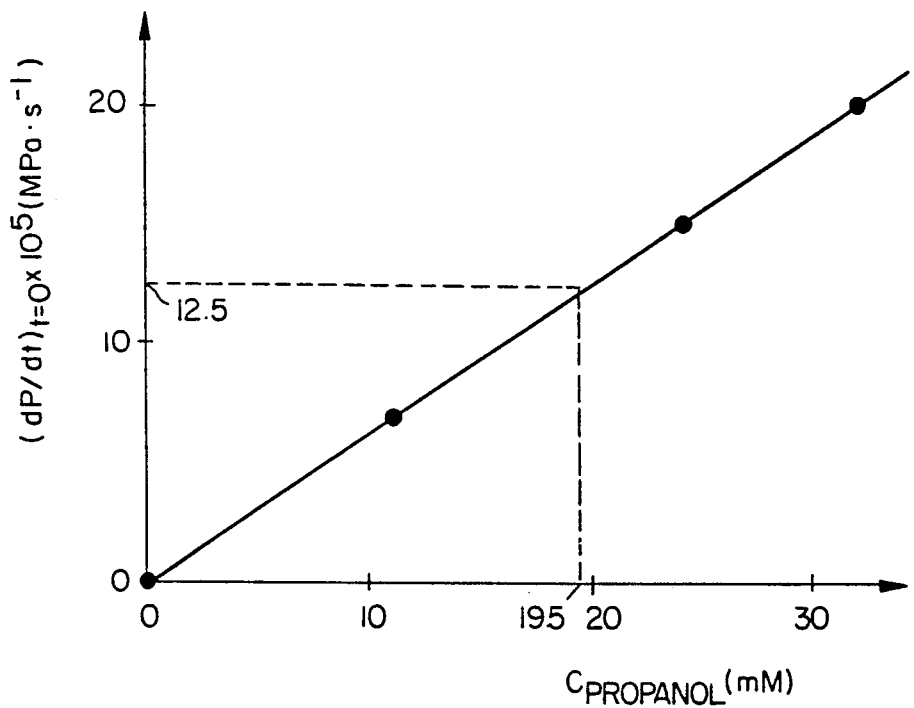
FIGS. 8B and 8C are $dP/dt$ vs. concentration plots derived from working embodiments set forth herein and illustrating a substantially linear relationship therebetween.
Figure 8C:
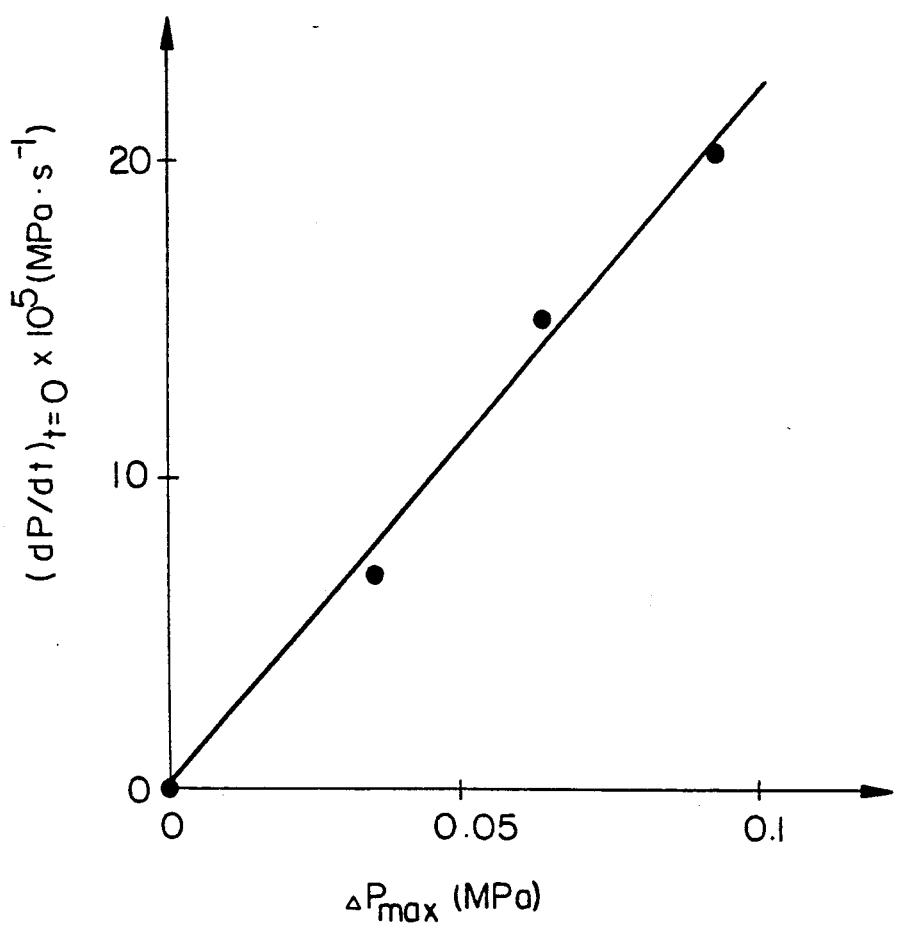

By calibration with known concentrations, the apparatus constant K is determined, as illustrated in FIGS. 8A and 8B. The calibration process yielded the following calibration points:

| $C_{Propanol}$(mM) | 11 | 24 | 32 |
|---|---|---|---|
| $(dP/dt)_{t=0} \cdot \times 10^5$ (MPa/s) | 6.86 | 15.06 | 20.31 |
| $\Delta P_{max}$(MPa) | 0.0344 | 0.0624 | 0.0928 | whereupon a $(dP/dt)_{t=0} = 12.5 \times 10^{-5}$ MPa s⁻¹ of a particular solution with an unknown concentration yielded a concentration of $C_{Propanol} = 19.5$ mM, as shown in FIG. 8B. FIG. 8C shows that $(dP/dt)_{t=0}$ and $\Delta P_{max}$ are linear functions of one another.

Figure 1:
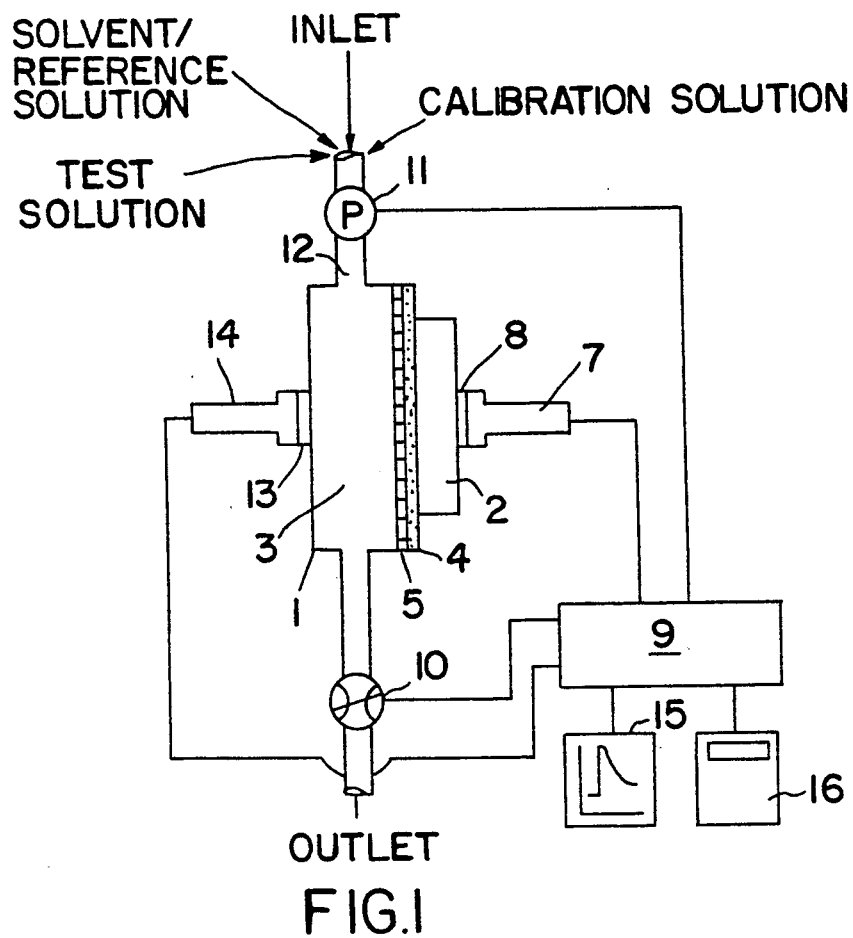
FIG. 1 is a schematic representation of a measurement apparatus for the execution of the process according to the invention.
Figure 9:
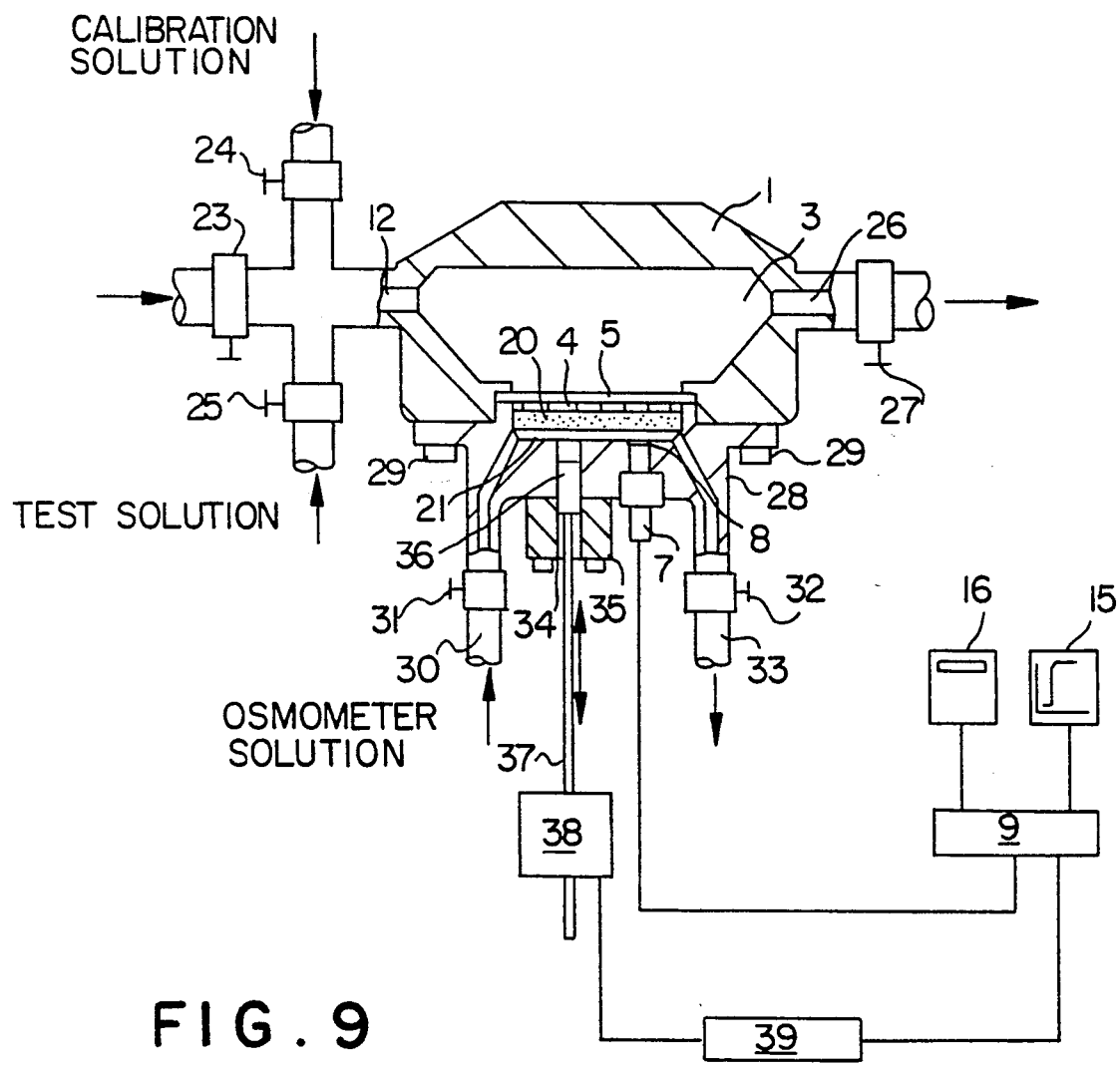
FIG. 9 is a sectional view of an apparatus for the execution of a process according to an alternative embodiment of the invention.

Referring now to FIG. 9, which is a sectional view of an apparatus for practice of an alternative embodiment of the invention, and which is similar to the apparatus shown in FIG. 1, inasmuch as it includes a solid enclosure or housing 1 having rigid pressure resistant walls, a housing 1 is internally divided into a measurement chamber 3 and an additional chamber 21, in which there is located a sealed osmosis cell 20, for example, an algae cell, an internodal cell made from characeen (or characeae, characin), a ceramic cell, or a cell comprising a glass sinter material, ceramic or plastic.

The measurement chamber 3 can, as a matter of choice, be supplied with water, a reference, a solvent, a calibration or a test solution through a pipe 12. To this end, there are provided valves 23, 24, and 25, which may be opened during the introduction of such fluids and then closed during the measurement phase of the process. Similarly, there is provided a valve 27 on the outlet side of the device through which these various fluids and solutions may exit. The provided arrows indicate preferred flow directions.

The osmosis cell 20 abuts against a membrane 4. Preferably, the osmosis cell 20 is reinforced via a support grid 5 so as to increase its coefficient of elasticity. This composite arrangement is tightly installed between housing 1 and an additional housing member 28, which is attached to housing 1 via screws 29. Preferably, an adequate sealer or gasket (not shown) is interposed between housing 1 and additional housing member 28.

Whereas the osmotic cell arrangement of FIG. 9 is basically similar to that described above with respect to FIG. 1, it will be understood to those skilled in the art that either of the alternate osmotic cell arrangements shown in FIGS. 2 and 3 could also be easily substituted for the osmotic cell arrangement shown in FIG. 9.

An osmotic solution is introduced into chamber 21 through a pipe 30, which includes an inlet valve 31 in an inlet pipe 30 and another valve 32 in an outlet pipe 33 to control the introduction and exchange of the osmotic solution. As noted above, the osmotic solution can also be introduced through the measurement chamber 3, in which case this additional osmometer solution supply means can be eliminated. Outlet pipe 33 could include means for establishing atmospheric pressure (or other pressures) within measurement chamber 3.

In contrast to the apparatus shown in FIG. 1, which is provided with pressuring measuring devices 7 and 14 for both of chambers 2 and 3, respectively, the apparatus shown in FIG. 9 is provided with only a single pressure measuring device 7, having an associated pressure sensor 8, for sensing the pressure in additional chamber 21 wherein osmotic cell 20 is located. To this end, pressure measuring device 7 is solidly anchored in housing member 28.

Additionally, and once again in contrast to the apparatus shown in FIG. 1, the apparatus in FIG. 9 is provided with an arrangement for varying the hydrostatic pressure existing in additional chamber 21 in which osmotic cell 20 is disposed. In this regard, there is provided a cylinder 34, the operational extension of which is elongated through the provision of a fixture 35 attached to housing member 28. A movable rod, piston or plunger 36 is positioned within cylinder 34 and is connected to an elongated push-pull rod 37 which interconnects piston 36 with an associated actuation unit 38.

Similar to the arrangement shown in FIG. 1, a centrally located computer unit 9 is provided with a display device 15 and a printer 16 and, additionally, electrical signals indicative of the hydrostatic fluid sensed by pressure measuring device 7. Moreover, central computer unit 9 preferably interfaces with the actuation unit 38 through a control circuit 39.

Preferably, as is the case with the apparatus shown in FIG. 1, the osmotic cell 20 of FIG. 9 has a high ratio of surface area to volume and a relatively high degree of rigidity due, in part, to the provision of a support grid 5.

Piston 36 is manipulated via actuation unit 38 and control circuit 39, such that the hydrostatic pressure acting on osmotic cell 21 can be either increased or decreased. During the measuring phase of the process, this pressure is manipulated via piston 36 in such manner that the volume (e.g., solvent) flow across the membrane is essentially maintained at zero. The positioning of piston 36 is controlled by computer 9 through control circuit 39 and actuation unit 38 and is interdependent to the currently measured pressure acting on osmotic cell 20 as sensed by the pressure measuring and transmitting devices 7 and 8.

If a solution having a known concentration is introduced into chamber 3, the hydrostatic pressure acting on the osmotic cell 20 is controlled via piston 36, such that the differential pressure flow with respect to time is maintained at substantially zero. That is, the rate of change of volume with respect to time is maintained at substantially zero. If a solution is then introduced into chamber 3 which has a higher concentration of a solute than this calibration solution or solution of known concentration, then the pressure acting on osmotic cell 20 is lowered by withdrawal of piston 36, such that the requirement that $dP/dt=0$ is substantially maintained, as is illustrated in FIG. 10b. Conversely, if a solution is introduced which has a lower concentration of solute, the hydrostatic pressure acting on osmotic cell 21 is correspondingly increased. Accordingly, this rate of change equal to zero condition explained immediately above is a variation of the process described above with respect to FIG. 1. However, only a single pressure measuring device need be employed.

Figure 10A:
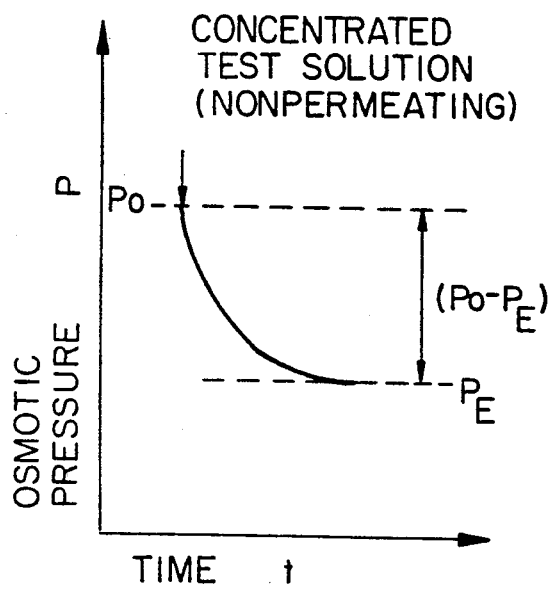
FIG. 10A and 10B are pressure vs. time plots showing the shorter measurement time achieved when measuring the concentration of nonpermeating substances according to this alternative embodiment of the invention.
Figure 10B:
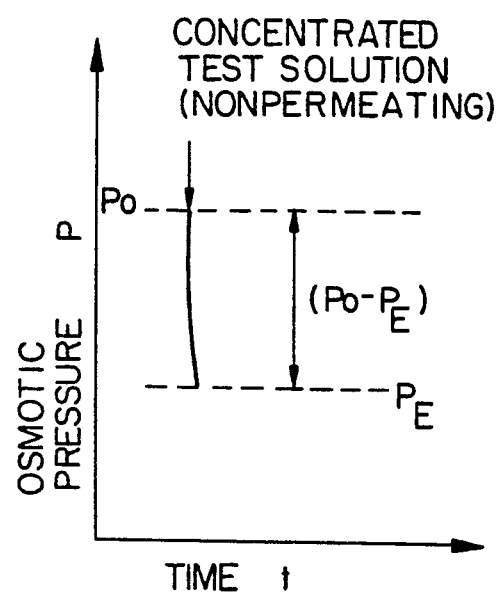

FIGS. 10a and 10b illustrate the decrease in time required for the measurement phase according to this alternative embodiment of the invention. In this regard, FIG. 10a illustrates the length of time required to obtain the pressure differential $(P_0-P_E)$ according to the process shown in U.S. Pat. No. 4,706,495, while FIG. 10b illustrates the considerably shorter time required to obtain this pressure differential measurement according to this alternative embodiment of the present invention.

The differential pressure change $(P_0-P_E)$ shown in FIGS. 10a and 10b is used to determine the change of concentration of a nonpermeating solute dissolved in a solvent, as compared with a known concentration determined from a reference or calibrating solution.

Figure 11:
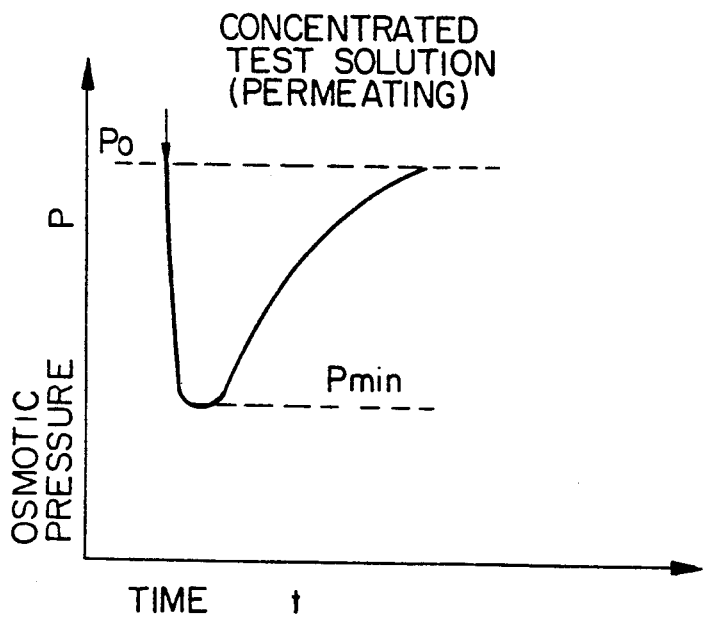
FIG. 11 is a pressure vs. time plot illustrating the use of this alternative embodiment of the invention to measure the concentration of a solution containing a permeating solute.

If a permeating solute is present, a similar method can be employed. The resulting pressure vs. time measurement curves are then two-phased, meaning that, during an increase of the concentration after the establishment of a minimum pressure, a solute migration phase takes place, which can be observed and the length of which cannot be influenced, as is shown in FIG. 11. In the case where the solution whose concentration is to be measured contains both a permeating solute, as well as a nonpermeating solute, there results a superposition effect, as already described above. [See, in this regard, FIG. 4C.]

The time required for the measurement phase of the process depends primarily on the response time of the osmotic cell, which is, in turn, controlled by the halftime of the solvent exchange. For example, the surface area to volume ratio and the coefficient of elasticity of the osmotic cell, as well as the hydraulic conductivity of the cell membrane should be, preferably, as great as possible. A controlling consideration is the maintenance of the rate of change of pressure with respect to time $(dP/dt)$ acting on the osmotic cell, which is maintained at substantially zero, in order that the pressure changes can be recorded as accurately as possible. The pressure measuring device 7 transmits electrical signals indicative of the pressure acting on osmotic cell 20. Preferably, these signals are either digital or converted to digital form and are evaluated by the computer 9. The resulting pressure vs. time curves may be displayed on display unit 15 and/or printed on printer 16, as a result of which the concentration(s) of the permeating and nonpermeating solutes can be established.

Computer 9, in turn, can forward the established pressure values to control unit 39, which, in turn, generates a control signal which activates actuation unit 38 to position push-pull rod 37 so as to appropriately vary the volume of the chamber containing the osmotic cell 20 via plunger 36. The regulation, according to this aspect of the invention, is conducted in a step by step fashion dependent upon the sensed hydrostatic pressure acting on the osmotic cell 20, until the flow of solvent through the membrane ceases, e.g., until this value is maintained substantially at zero. Of course, similar to the arrangement shown in FIG. 1, an additional pressure measuring device (e.g., pressure measuring device 13 and 14) may be provided to sense the pressure existing in the measurement chamber.

Methods by which the pressure indicative signals generated by pressure measuring device 7 may be used to control the positioning of piston 36 so as to fulfill the condition that the differential pressure flow with respect to time is maintained at substantially 0 are well known to those versed in the art of error feedback control and are not discussed at length herein. It is well known that an error signal, indicative of a deviation from a desired condition, may be utilized, either in digital or analog form, to generate corrective signals. Additionally, it is well known that either the basic error signal or a signal derived therefrom, such as, for example, an integral of the basic error signal, may be used.

In summary, in one aspect, the invention features a process for the determination of the concentration of a substance dissolved in a solvent by the use of an osmometer. The osmometer comprises a two-chamber system with an osmosis cell and a pressure measurement apparatus to measure the hydrostatic pressure in the one chamber having rigid walls, into which either osmometer solutions or pure solvent can be fed or removed by an arrangement of feed and discharge lines, and with a second chamber also having rigid walls, in which either measurement solutions to be tested, or solvent, reference or calibration solutions can be fed or removed by an arrangement of feed and discharge lines, between which chambers a membrane is interposed, by which the osmometer solution in the osmosis cell is placed in communication with the solution in the second chamber 3, whereby the exchange of the substances to be measured occurs at different rates. This is characterized by the fact that the solvent, reference or calibration solution in the second chamber 3 is replaced by a measurement solution, and that, by the use of the pressure measurement apparatus 7, 8 in the first chamber 2, the pressure is measured in the osmosis cell, which has an incompressible membrane arrangement 4, 5, 6, 5A, 5B, and that the pressure in the second chamber 3 is varied so that the pressure in the osmosis cell 17, 18 remains constant during the measurement of the pressure as a function of time in the second chamber 3 with a pressure measurement apparatus 13, 14. The pressure curve is measured with the pressure measurement apparatus 13, 14, which is a yardstick for the concentrations of the nonpermeating and permeating substances, or the value of which is proportional to the flows of the permeating substances of the measurement solution between the osmosis cell 2 and the second chamber 3, and is displayed by an indicator apparatus or is evaluated in an evaluation circuit.

In preferred embodiments, at atmospheric pressure or an artificially generated working pressure, a constant working pressure is established by introducing the osmometer solution or the pure solvent either by direct input or by input into the second chamber. The solution in the second chamber is replaced by the measurement solution. The pressure in the second chamber is varied so that the propulsion force for the volume flow through the membrane is just compensated. The compensation pressure established in the second chamber is measured, whereby the compensating maximum pressure level reached in the second chamber is proportional to the concentration of the permeating and nonpermeating substances in the measurement solution, and decreases according to the concentration of permeating substances exponentially with the differential curve to the original pressure level or to the constant pressure level which is proportional to the concentration of the nonpermeating substances. The concentration of the nonpermeating substances and/or of the permeating substances is determined from the maximum pressures on the basis of calibration values or from the following relationship:

Nonpermeating substance: $\Delta P = \pi = R \cdot T \cdot C$, where $\pi$ is the osmotic pressure, C is the concentration, R = 8.31434 J/°K mol and T is the absolute temperature.

Permeating substance: $\Delta P = \sigma \cdot \pi$ where $\sigma$ is the coefficient of reflection of the substance. The working pressure in the osmosis cell is set to an underpressure or to a negative pressure in relation to atmospheric pressure and in relation to the pressure in the second chamber before the introduction of the measurement solution. For the determination of the concentrations of the individual permeating substances, the corresponding exponential functions of the differential curve are digitized and processed in a computer, and for an analysis of the substances are compared to the previously stored values of curves of known substances. During the measurement, the two-chamber system of the osmometer, the osmometer solution and the reference and calibration solution and the measurement solution are set to a defined temperature level and held there. The osmometer solution used is a pure solvent or a solvent which contains substances which are contained in the reference solution and in the measurement solution to be tested.

Another aspect of the invention resides broadly in an apparatus for the determination of the concentration of a substance dissolved in a solvent for the execution of the above-mentioned process with a first chamber 2 in which there are an osmosis cell 17, 18 and a pressure measurement apparatus 7, 8, with an inlet or outlet valve for the feed or discharge line of the osmometer solution, and a second chamber 3 with inlet and outlet valves 10 for the feed and discharge line for a reference, calibration or measurement solution and/or osmometer solution or a pure solvent. The apparatus includes a rigid osmosis cell 17, 18, with a membrane 4, 6 which is either supported by a rigid support grid 5, 5A, 5B and/or is placed in firm contact with it by an underpressure or by a negative pressure in the osmosis cell 17, 18. Also included are a valve arrangement 10 in the feed and discharge lines 12 of the measurement chamber 3, by which, before the measurement process, measurement solution can be fed in or extracted to vary the pressure in the measurement chamber 3, or an adjustment apparatus to vary the pressure by changing the volume of the second chamber 3, and a pressure measurement apparatus 13, 14 for the determination of the instantaneous pressure in the measurement chamber 3 and for the determination of the pressure curve during the time the substances to be tested are being exchanged. There is a control apparatus 9 for the valve and pump control 11 to increase the pressure in the measurement chamber 3 or for the adjustment apparatus and also a measurement apparatus 7, 8, 9 which determines the pressure decrease during the volume flow out of the osmosis cell 17, 18 into the latter, and determines a proportional actuating variable which controls either the valve control apparatus 10 in the feed and discharge lines of the measurement cell or a pressure increase apparatus 11 (pump) in the feed line 12 or the volume adjustment apparatus such that the force of the volume flow is compensated, whereby the working pressure in the second chamber 3 also remains constant, at least for a short time, during a maximum when the valves 10 in the feed and discharge lines of the measurement chamber 3 are closed. The osmosis cell consists of an incompressible porous body, saturated with solution, of glass sinter material, ceramic, plastic, or a solution film supported on both sides by a support grid. The membrane is a hyperfiltration membrane or a hollow fiber membrane. The pressure measurement apparatus 7, 8; 13, 14 in the first chamber 2 is an electrical pressure transformer which converts the hydrostatic pressure measured into an electrical analog or digital measurement which can be evaluated. The measurement devices are connected with the inputs of a computer 9, and the computer, on the basis of stored programs, determines the actuating variables for the pressure regulator to compensate for the concentration-dependent force during the exchange of the solvent or the permeating substances of the osmometer solution, and the values of the pressure curve in the second chamber are stored and evaluated, whereby the latter values can be represented or expressed as a curve by an arrangement of connected display devices 15. The osmosis cell 17, 18 has a layer density of $\leq 0.2$ mm.

In an alternative embodiment, the invention features the procedure for the determination of the content of a substance dissolved in a solution via an osmometer, consisting of a two-chamber system with an osmosis cell and a pressure measuring device to measure the hydrostatic pressure in a chamber which has rigid walls. Through the in-and-outlets of this chamber the osmometer solution can be added or removed through an in-and-outlet. Between these chambers there is a membrane by which the osmotic solution contained in the osmotic cell contacts the second chamber where an exchange of the solution to be measured takes place with various speed. It (process) is characterized by the fact that the solution, reference solution and calibration solution contained in the second chamber 3 are exchanged against a measuring solution, so that pressure measuring device 7, 8 can measure the pressure in the osmotic cell located in the first chamber 21, (FIG. 9) in such a manner, that the pressure in the first chamber 21, (FIG. 9) is varied so that the propelling power for the flow of volume through the membrane is compensated and that the pressure measurement device 7, 8 produces a measured pressure curve, which is a measure of the concentration of the nonpermeating and permeating materials, that is, their value is proportional to the flow of the permeating substance or materials of the calibration solution between the osmosis cell 20, (FIG. 9) and the second chamber 3 and can be indicated by a measuring device or an evaluation circuitry 20, (FIG. 9).

Preferably, the process is characterized by the following steps: (a) Osmosis cell 20 will build up a working pressure by atmospheric pressure or artificially generated work pressure through the addition of osmometer solution or clear solution through either direct insertion or insertion through the second chamber 3; b) the solution, which is to be found in chamber 3, will be exchanged against the calibrating solution; c) the pressure in the first chamber 21 is variated in such a manner that the propelling power for the volume flow through the membrane is compensated so that small dp/dt, equals 0; d) the compensation pressure in the first chamber is being measured continuously whereby the attained maximal pressure level in the first chamber 21 is proportional to the concentration of the permeating and nonpermeating substances in the test solution, in relation with the differential curve chart to the original pressure level, or it falls back of to the constant pressure level which is proportionate to the content of the nonpermeating solution.

In this alternative embodiment, the invention also features a device or apparatus for determination of the content of substances dissolved in a solution where the first chamber 21 in which an osmosis cell 20 and a sensor 8 of a pressure sensing device 7 are matched and incorporated so that an inlet and outlet exists for the addition or removal of the osmometer solution and with a second chamber 3 with the inlet and outlet for a calibration or reference solution or measurement solution and/or osmometer solution or pure solution respectively characterized by rigid osmosis cell 20 which has thin walls. It displays a spacious relationship between the surface and the volume content, with a membrane 4 which lies upon the osmosis cell 20, a control unit 38, 37, 39 for the variances of the pressure through the change of the volume of the first chamber 21 and a pressure measuring apparatus 9, 7, 8 for the determination of the instantaneous pressure in the first chamber 21 and for the determination of the pressure curve during the time the substances to be tested are exchanged. There is a relationship of the determined pressure flow and a servoaction will occur in control unit 37, 38, 39 for the variation of pressure in the first chamber 21.

Still another alternative embodiment of the invention features the apparatus characterized by the fact that the adjustment device for the variation of the pressure within the first chamber 21 consists of a movable plunger piston 36 which can be moved by either pressure, or mechanically with a motor, or can be manually moved by an adjustment to which it is attached (FIG. 9).

Preferably, the apparatus is characterized by the fact that an electronic switching mechanism 39 is planned, which would control an electric motor or a hydraulic control source whose movement would be transferred to control rod number 36. [See Figure number 9].

The invention as described hereinabove in the context of a preferred embodiment is not to be taken as limited to all of the provided details thereof, since modifications and variations thereof may be made without departing from the spirit and scope of the invention.

What is claimed is:

1. A process for testing a test solution, said test solution comprising a solvent and at least one solute dissolved in said solvent, said process employing a first chamber defining a first volume, a second chamber defining a second volume, said first volume being less than said second volume and a membrane interposed between said first and second chambers, said process comprising the steps of:
  (a) introducing an osmometer solution into said first chamber;
  (b) introducing a reference solution into said second chamber;
  (c) determining a reference pressure $P_0$ established in one of said first and second chambers;
  (d) replacing said reference solution in said second chamber with said test solution;
  (e) limiting the amount of fluid exchange between said first and second chambers to a value equalling approximately zero;
  (f) limiting the amount of deflection of said membrane to a preselected value;
  (g) maintaining a constant fluid pressure in one of said first and second chambers;
  (h) determining at least one pressure change characteristic occurring in the other of said first and second chambers; and
  (i) using said at least one determined pressure change characteristic to determine the concentration of said at least one solute dissolved in said solvent.

2. The process according to claim 1, wherein said one of said first and second chambers in which said fluid pressure is maintained constant in said first chamber containing said osmometer solution, and wherein the other of said first and second chambers in which said at least one pressure change characteristic is determined in said second chamber containing said test solution.

3. The process according to claim 2, wherein said membrane is maintained in a substantially nondeflectable configuration.

4. The process according to claim 2, wherein said at least one pressure change characteristic comprises a maximum pressure change $\Delta P_{max}$ which substantially corresponds to the difference between said reference pressure $P_0$ in said second chamber when said second chamber contains said reference solution and the fluid pressure in said second chamber substantially immediately following the replacement of said reference solution with said test solution.

5. The process according to claim 4, wherein said solute dissolved in said solvent comprises at least one of:
  (1) a nonpermeating substance;
  (2) a permeating substance;
  (3) a mixture of a nonpermeating substance and a permeating substance; and
  (4) at least two permeating substances; and
wherein said nonpermeating substances are substances which have relatively low degree of permeability with respect to said membrane, as compared to said permeating substances which are substances having a relatively high degreee of permeability with respect to said membrane.

6. The process according to claim 5, wherein said solute consists of said mixture of said nonpermeating substance and said permeating substance 3, and;
  wherein said determination of concentration in step (i) comprises at least one of:
    (a) determining the combined concentration of said nonpermeating substance and said permeating substance through a relationship wherein said combined concentration is proportional to said maximum pressure change $\Delta P_{max}$; and
    (b) determining a substantially stable final pressure in said second chamber and determining the individual concentration of said nonpermeating substance through a relationship wherein said individual concentration of said nonpermeating substance is proportional to the difference between said substantially stable final pressure and said reference pressure $P_0$.

7. The process according to claim 5, wherein said determination of concentration in step (i) comprises at least one of:
  (a) determining the concentration of said nonpermeating substance according to the relationship:

$$\Delta P = \pi = R \cdot T \cdot C, \qquad \text{(Equation 1)}$$

wherein
  $\pi$ is the osmotic pressure,
  C is the concentration,
  R = 8,31434 J/°K mol, and
  T is the absolute temperature; and
  (b) determining the concentration of said permeating substance according to the relationship:

$$\Delta P = \sigma \cdot \pi, \qquad \text{(Equation 2)}$$

wherein $\sigma$ is the coefficient of reflection of said permeating substance.

8. The process according to claim 7, wherein said solute consists of said mixture of permeating substances in item (4), wherein a first of said at least two permeating substance has a relatively higher degree of permeability with respect to said membrane than a second of said at least two permeating substances, and wherein said determination of concentration in step (i) further comprises at least one of:
  (a) determining a pressure change $\Delta P^S$ associated with the passage of said first permeating substance through said membrane;
  (b) determining the concentration of said first permeating substance according to Equation 2;
  (c) determining a pressure change $\Delta P^F$ associated with the passage of said second permeating substance through said membrane; and
  (d) determining the concentration of said second permeating substance according to Equation 2.

9. The process according to claim 8, wherein:
  at least one of said first chamber and said second chamber employs at least one rigid wall;
  said membrane is generally incompressible;
  pressure $P_O$ is a constant hydrostatic working pressure;
  said maintaining of constant fluid pressure in step (g) adjusts the propulsion force for the volume of flow through said membrane; and
  at least one of said $\Delta P^S$ and $\Delta P^F$ occurs at an exponential rate.

10. The process according to claim 2, wherein said maintaining of a constant fluid pressure in said first chamber in step (e) is carried out by varying at least one of: (a) the fluid pressure in said second chamber, and (b) the volume of said second chamber.

11. The process according to claim 2, wherein said solute comprises a substance with respect to which said membrane is relatively permeable, and wherein said concentration determination in step (i) comprises:
  (a) determining at least an approximate value of the rate of change of the fluid pressure in said second chamber with respect to time (dP/dt) at substantially the time of replacement of said reference solution in said second chamber with said test solution (t=0); and (b) determining the concentration of said substance through a relationship wherein the concentration of said substance is proportional to said rate of change (dP/dt) at said time (t=0).

12. The process according to claim 2, further comprising the additional step of inducing, in said first chamber, a fluid pressure which is one of a negative pressure and a pressure which is less than the ambient atmospheric pressure prior to the replacement of said reference solution in said second chamber with said test solution.

13. The process according to claim 2, further comprising the additional step of inducing, in said first chamber, a fluid pressure which is less than the fluid pressure in said second chamber prior to the replacement of said reference solution in said second chamber with said test solution.

14. The process according to claim 2, wherein said pressure change characteristic determination in step (h) comprises sensing, digitizing and storing in memory values representative of the fluid pressure in said second chamber for a period of time following the replacement of said reference solution in said second chamber with said test solution, and wherein said concentration determination in step (i) comprises comparing said sensed, digitized and stored values with determination criteria previously stored in memory.

15. The process according to claim 14, wherein said determination criteria comprise sensed, digitized and stored values representative of the fluid pressure in said second chamber following replacement of said reference solution with at least one solution having a known concentration of said solute.

16. The process according to claim 2, wherein said first and second chambers are maintained at a constant temperature.

17. The process according to claim 2, wherein said reference solution consists of at least one of said solvent and said solvent having said solute dissolved therein, and wherein said osmometer solution consists of at least one of said solvent and said solvent having said solute dissolved therein.

18. A process for the determination of the concentration of a solution to be tested comprising at least one substance dissolved in a solvent, said process comprising the steps of:

(a) providing a first chamber defining a first volume and a second chamber defining a second volume, said first volume being less than said second volume;

(b) interfacing said first and second chambers through a membrane;

(c) introducing an osmometer solution into said first chamber;

(d) introducing the solution to be tested into said second chamber;

(e) limiting the amount of fluid exchange between said first and second chambers to a value equalling approximately zero;

(f) limiting the amount of deflection of said membrane to a preselected value;

(g) maintaining a constant fluid pressure in one of said first and second chambers;

(h) determining at least one pressure change characteristic occurring in the other of said first and second chambers; and (i) using said at least one determined pressure change characteristic to determine the concentration of the at least one substance dissolved in the solvent.

19. The process according to claim 18, further comprising the additional steps of calibrating the process by introducing a calibration solution into said second chamber, and determining at least one pressure change characteristic occurring in the other of said first and second chambers in response thereto.

20. The process according to claim 19, wherein:
at least one of said first chamber and said second chamber employs at least one rigid wall; and
said maintaining of constant fluid pressure in step (g) adjusts the propulsion force for the volume of flow through said membrane.

21. An apparatus for the determination of the concentration of a solute dissolved in a solvent, said apparatus comprising:
a first chamber defining a first volume;
a second chamber defining a second volume, said first volume being less than said second volume;
a membrane interposed between said first and second chambers;
means for introducing an osmometer solution into said first chamber;
means for introducing, selectively, into said second chamber, a reference solution and said solute dissolved in said solvent;
means for limiting the amount of fluid exchange between said first and second chambers to a value equalling approximately zero;
means for limiting the amount of deflection of said membrane to a preselected value;
pressure maintenance means for maintaining a constant pressure in one of said first and second chambers; and
pressure sensor means for sensing the fluid pressure in the other of said first and second chambers.

22. The apparatus according to claim 21, wherein said pressure sensor means senses the fluid pressure in said second chamber, wherein said pressure maintenance means maintains a constant pressure in said first chamber, and further comprising another pressure sensor means for sensing the fluid pressure in said first chamber and deflection prevention means for preventing any substantial deflection of said membrane.

23. The apparatus according to claim 22, wherein said pressure maintenance means comprises:
pressure/volume varying means for varying at least one of: the pressure of said second chamber and the volume of said second chamber; and
control means for receiving signals from said another pressure sensor means indicative of the fluid pressure in said first chamber, and for activating said pressure/volume varying means in response thereto.

24. The apparatus according to claim 23, wherein said means for introducing, selectively, into said second chamber, said reference solution and said solute dissolved in said solvent comprises a feed line, a discharge line, pump means disposed in one of said feed line and said discharge line, and valve means disposed in the other of said feed line and said discharge line.

25. The apparatus according to claim 24, wherein said pressure sensor means comprises means for generating digitized signals representative of the fluid pressure in said second chamber, and wherein said control means comprises a computer, said computer including means for receiving and storing said digitized signals in a time ordered sequence.

26. The apparatus according to claim 25, further comprising display means for displaying said digitized signals.

27. The apparatus according to claim 26, wherein:
at least one of said first chamber and said second chamber employs at least one rigid wall; and
said maintaining of constant fluid pressure adjusts the propulsion force for the volume of flow through said membrane.

28. The apparatus according to claim 21, wherein said membrane comprises at least one of: a substantially incompressible porous body saturated with solution; and glass sinter material; a solution film interposed between at least two support grids; a hyperfiltration membrane; and a wood membrane.

29. The apparatus according to claim 28, further comprising an osmosis cell located within said first chamber, said osmosis cell having a layer thickness of 0.2 mm.

30. A process for the determination of the concentration of a test solution, said test solution comprising at least one solute dissolved in a solvent, said process employing a first chamber defining a first volume, a second chamber defining a second volume, said first volume being less than said second volume, a membrane interposed between said first and second chambers, compensation means for compensating for the volume flow of at least said solvent through said membrane and between said first and second chambers, and pressure sensing means for sensing at least one pressure existing in said first chamber, said process comprising the steps of:
introducing an osmometer solution into said first chamber;
introducing a reference solution into said second chamber;
determining a reference pressure $P_0$ established in one of said first and second chambers;
replacing said reference solution in said second chamber with said test solution;
limiting the amount of fluid exchange between said first and second chambers to a value equalling approximately zero;
limiting the amount of deflection of said membrane to a preselected value;
employing said compensation means for compensating for the volume flow of at least said solvent through said membrane;
employing said pressure sensing means for determining at least one pressure change characteristic occurring in said first chamber; and
using said at least one determined pressure change characteristic occurring in said first chamber to determine the concentration of said at least one solute dissolved in said solvent.

31. A process according to claim 30, wherein said compensation means comprises means for varying the volume of said first chamber and wherein said step of employing said compensation means comprises varying the volume of said first chamber to compensate for the volume flow of at least said solvent through said membrane.

32. A process according to claim 30, wherein said compensation means comprises means for varying the hydrostatic pressure existing in said first chamber and wherein said step of employing said compensation means comprises varying the hydrostatic pressure existing in said first chamber to compensate for the volume flow of at least said solvent through said membrane.

33. The process according to claim 30, wherein said at least one solute comprises a substance with respect to which said membrane is relatively nonpermeable, and wherein said at least one determined pressure change characteristic occurring in said first chamber comprises a maximum pressure change differential ($P_O - P_E$) between the pressure in said first chamber when said second chamber contains said reference solution ($P_O$) and the pressure in said first chamber when said second chamber contains said test solution ($P_E$).

34. The process according to claim 30, wherein said at least one solute comprises a substance with respect to which said membrane is relatively permeable, and wherein said at least one determined pressure change characteristic occurring in said first chamber comprises a maximum pressure change differential ($P_O - P_{min}$) between the pressure in said first chamber when said second chamber contains said reference solution ($P_O$) and the peak pressure in said first chamber when said second chamber contains said test solution ($P_{min}$).

35. The process according to claim 30, wherein:
at least one of said first chamber and said second chamber employs at least one rigid wall; and
said pressure $P_O$ is a constant hydrostatic working pressure.

36. An apparatus for the determination of the concentration of a test solution, said test solution comprising a solute dissolved in a solvent, said apparatus comprising:
a first chamber defining a first volume;
a second chamber defining a second volume, said first volume being less than said second volume;
a membrane interposed between said first and second chambers;
means for introducing an osmometer solution into said first chamber;
means for introducing, selectively, into said second chamber, a reference solution and said test solution;
means for limiting the amount of fluid exchange between said first and second chambers to a value equalling approximately zero;
means for limiting the amount of deflection of said membrane to a preselected value;
pressure sensing means for sensing the pressure existing in said first chamber and for generating signals representative thereof; and
compensation means for compensating for the volume flow of at least said solvent through said membrane and between said first and second chambers.

37. An apparatus according to claim 36, wherein said compensation means comprises means for varying the hydrostatic pressure existing in said first chamber.

38. An apparatus according to claim 36, wherein said compensation means comprises means for varying the volume of said first chamber.

39. An apparatus according to claim 36, wherein said compensation means comprises a reciprocally translatable piston which can be extended into and withdrawn from said first chamber, and means for translating said piston in response to said pressure representative signals generated by said pressure sensing means.

40. The apparatus according to claim 36, wherein:
at least one of said first chamber and said second chamber employs at least one rigid wall.

* * * * *

UNITED STATES PATENT AND TRADEMARK OFFICE
CERTIFICATE OF CORRECTION

PATENT NO. : 5,005,403

DATED : April 9, 1991

INVENTOR(S) : Ernst STEUDLE and Burkhard STUMPF

It is certified that error appears in the above-identified patent and that said Letters Patent is hereby corrected as shown below:

In column 11, line 28, after 'corresponds', insert --to--.

In column 12, line 48, after 'that', delete "$(dP/dt)_{t=}0$" and insert --$(dP/dt)_{t=0}$--.

Column 19, In Claim 5, line 54, after 'have', insert --a--.

Column 23, In Claim 28, lines 17-18, after solution;', delete "and", and insert -- a--

UNITED STATES PATENT AND TRADEMARK OFFICE
CERTIFICATE OF CORRECTION

PATENT NO. : 5,005,403
DATED : April 9, 1991
INVENTOR(S) : Ernst STEUDLE and Burkhard STUMPF It is certified that error appears in the above-identified patent and that said Letters Patent is hereby corrected as shown below:

In Figure 5B, please delete "107mM" and insert --10.7 mM--.

In Figure 7B, please delete "$\Delta P^F_{max}$ (MPa)" and insert --$\Delta P^S_{max}$ (MPa)--.

In Figure 8B, please delete "195" and insert --19.5--.

In Figure 10A, please extend the pressure time curve, as indicated on the enclosed newly presented drawings.

In Figure 10B, please extend the osmotic pressure curve, as indicated on the enclosed newly presented drawings.

In Figure 11, please extend the pressure time curve, as indicated on the enclosed newly presented drawings.

Signed and Sealed this

First Day of December, 1992

Attest:

DOUGLAS B. COMER

*Attesting Officer*   *Acting Commissioner of Patents and Trademarks*